United States Patent [19]

Borzatta et al.

[11] Patent Number: 5,194,466

[45] Date of Patent: Mar. 16, 1993

[54] PIPERIDINE-TRIAZINE COMPOUNDS FOR USE AS STABILIZERS FOR ORGANIC MATERIALS

[75] Inventors: Valerio Borzatta, Bologna; Franca Masina, Anzola Emilia, both of Italy

[73] Assignee: Ciba-Geigy Corporation, Ardsley, N.Y.

[21] Appl. No.: 810,658

[22] Filed: Dec. 19, 1991

Related U.S. Application Data

[62] Division of Ser. No. 511,143, Apr. 19, 1990.

[30] Foreign Application Priority Data

Jul. 27, 1989 [IT] Italy .................. 20285 A/89

[51] Int. Cl.$^5$ .................................................. C08K 5/34
[52] U.S. Cl. ...................................... 524/101; 524/100
[58] Field of Search ............................ 524/100, 101

[56] References Cited

U.S. PATENT DOCUMENTS

| | | | |
|---|---|---|---|
| 3,925,376 | 12/1975 | Chalmers et al. | 524/100 |
| 4,108,829 | 8/1978 | Cassandrini et al. | 524/100 |
| 4,433,145 | 2/1984 | Wiezer et al. | 524/100 |
| 4,533,688 | 8/1985 | Yoda et al. | 524/100 |
| 4,740,544 | 4/1988 | Nakahara et al. | 524/100 |

FOREIGN PATENT DOCUMENTS

| | | |
|---|---|---|
| 117229 | 8/1984 | European Pat. Off. . |
| 176106 | 4/1986 | European Pat. Off. . |
| 299925 | 1/1989 | European Pat. Off. . |

OTHER PUBLICATIONS

Derwent Abst. 86-248801/38 (1986).

*Primary Examiner*—Johann Richter
*Attorney, Agent, or Firm*—Luther A. R. Hall

[57] ABSTRACT

Piperidine-triazine compounds of the general formula (I)

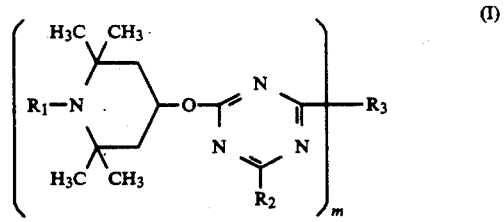

in which $R_1$ is e.g. hydrogen or methyl, $R_2$ is e.g. 2,2,6,6-tetramethyl-4-piperidyloxy or 1,2,2,6,6-pentamethyl-4-piperidyloxy, m is e.g. 2, 3 or 4 and, if m is 2, $R_3$ is e.g. a group of the formula (IIIc) or (IIIe)

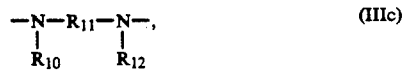

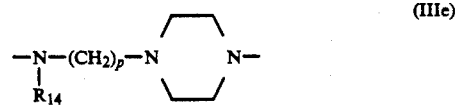

in which $R_{10}$ and $R_{12}$ which can be identical or different are e.g. hydrogen, cyclohexyl, 2,2,6,6-tetramethyl-4-piperidyl or 1,2,2,6,6-pentamethyl-4-piperidyl, $R_{11}$ is e.g. $C_2$–$C_6$alkylene, $R_{14}$ is e.g. hydrogen or methyl and p is e.g. 2, and, if m is 3 or 4, $R_3$ is e.g. a group of the formula (IV)

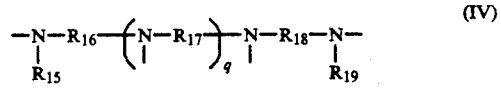

in which $R_{15}$ and $R_{19}$ which can be identical or different are e.g. hydrogen, 2,2,6,6-tetramethyl-4-piperidyl or 1,2,2,6,6-pentamethyl-4-piperidyl, $R_{16}$, $R_{17}$ and $R_{18}$ which can be identical or different are e.g. $C_2$–$C_3$alkylene and q is e.g. zero or 1, are effective as light stabilizers, heat stabilizers and oxidation stabilizers for organic materials.

13 Claims, No Drawings

PIPERIDINE-TRIAZINE COMPOUNDS FOR USE AS STABILIZERS FOR ORGANIC MATERIALS

This is a divisional of Ser. No. 511,143 filed Apr. 19, 1990.

The present invention relates to novel piperidine-triazine compounds, to their use as light stabilizers, heat stabilizers and oxidation stabilizers for organic materials, in particular synthetic polymers, and to organic materials thus stabilized.

It is known that synthetic polymers are subject to photooxidative degradation when they are exposed to sunlight or other sources of ultraviolet light in the presence of oxygen. For their use in practice, it is therefore necessary to add to them suitable light stabilizers, such as certain benzophenone or benzotriazole derivatives, nickel complexes, substituted benzoic acid esters, alkylidenemalonates, cyanoacrylates, aromatic oxamides or sterically hindered amines.

Some triazine compounds containing 2,2,6,6-tetramethylpiperidine groups and their use as light stabilizers, heat stabilizers and oxidation stabilizers for synthetic polymers have been reported in U.S. Pat. No(s). 4,108,829, 4,433,145, 4,533,688 and 4,740,544, in European Patent Applications No(s). 176,106 and 199,925 and Japanese Patent Kokai No. 61/176,662.

The present invention relates to novel compounds of the general formula (I)

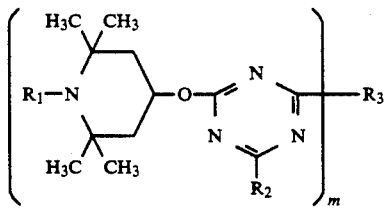

in which $R_1$ is hydrogen, $C_1$–$C_8$alkyl, O·, OH, NO, $CH_2CN$, $C_1$–$C_{18}$alkoxy, $C_5$–$C_{12}$cycloalkoxy, $C_3$–$C_6$alkenyl, $C_7$–$C_9$phenylalkyl which is unsubstituted or mono-, di- or tri-substituted on the phenyl by $C_1$–$C_4$alkyl, $C_1$–$C_8$acyl or $C_2$–$C_4$alkyl substituted by OH in the 2-, 3- or 4-position, $R_2$ is a group $-OR_4$, $-SR_4$ or

wherein $R_4$ is $C_1$–$C_{18}$alkyl, $C_5$–$C_{12}$cycloalkyl which is unsubstituted or mono-, di- or tri-substituted by $C_1$–$C_4$alkyl, phenyl which is unsubstituted or mono-, di- or tri-substituted by $C_1$–$C_4$alkyl, $C_7$–$C_9$phenylalkyl which is unsubstituted or mono-, di or tri-substituted on the phenyl by $C_1$–$C_{18}$alkyl, $C_3$–$C_{18}$alkyl interrupted by 1, 2 or 3 oxygen atoms, $C_2$–$C_4$alkyl substituted in the 2-, 3- or 4-position by di-($C_1$–$C_4$alkyl)-amino, or a group of the formula (II)

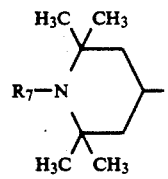

where $R_7$ is as defined for $R_1$, and $R_5$ and $R_6$ which can be identical or different are hydrogen, $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$alkyl, $C_2$–$C_4$alkyl substituted in the 2-, 3- or 4-position by $C_1$–$C_8$alkoxy or by di-($C_1$–$C_4$alkyl)-amino, or a group of the formula (II), or the group

is a heterocyclic ring having 5–7 members, m is an integer from 2 to 6, and, if m is 2, $R_3$ is one of the groups of the formula (IIIa)–(IIIe)

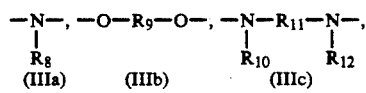

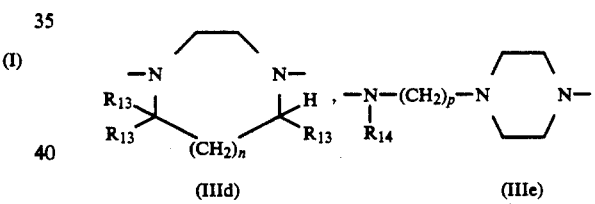

in which $R_8$, $R_{10}$, $R_{12}$ and $R_{14}$ which can be identical or different are hydrogen $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di- or tri-substituted on the phenyl by $C_1$–$C_4$-alkyl, or a group of the formula (II), $R_9$ is $C_2$–$C_{12}$ alkylene, cyclohexylene, cyclohexylenedimethylene, methylenedicyclohexylene, isopropylidenedicyclohexylene, phenylene or xylylene, $R_{11}$ is as defined for $R_9$ or is $C_4$–$C_{12}$alkylene interrupted by 1, 2 or 3 oxygen atoms, $R_{13}$ is hydrogen or methyl, n is zero or 1 and p is an integer from 2 to 6, and, if m is 3, 4, 5 or 6, $R_3$ is a group of the formula (IV)

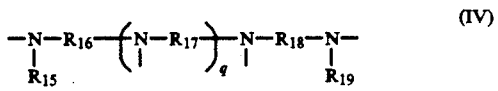

in which $R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and if m is 3, $R_3$ is also a group of the formula (Va) or (Vb)

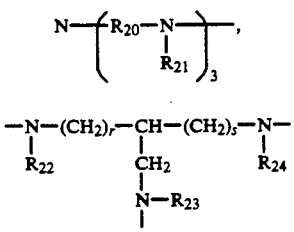

(Va)

$$-N-(CH_2)_r-CH-(CH_2)_s-N- \atop {\overset{|}{R_{22}}} \quad {\overset{|}{\underset{\underset{R_{23}}{|}}{\overset{|}{CH_2}}{N}}} \quad {\overset{|}{R_{24}}}$$

(Vb)

in which $R_{20}$ is $C_2$–$C_6$alkylene, $R_{21}$, $R_{22}$, $R_{23}$ and $R_{24}$ which can be identical or different are as defined for $R_8$, and r and s which can be identical or different are integers from 2 to 6.

Representative examples of $C_1$–$C_8$alkyl $R_1$ and $R_7$ are methyl, ethyl, propyl, butyl, isobutyl, pentyl, hexyl, heptyl and octyl. $C_1$–$C_4$alkyl, in particular methyl, is preferred.

Examples of $C_1$–$C_{18}$alkyl are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl. $C_1$–$C_8$Alkyl is preferred.

Representative examples of $C_2$–$C_4$alkyl $R_1$ and $R_7$ substituted by OH are 2-hydroxyethyl, 2-hydroxypropyl, 3-hydroxypropyl, 2-hydroxybutyl and 4-hydroxybutyl. 2-hydroxyethyl is preferred.

Preferred examples of $C_2$–$C_4$alkyl $R_5$ and $R_6$ substituted by $C_1$–$C_8$alkoxy are 2-methoxyethyl, 2-ethoxyethyl, 3-methoxypropyl, 3-ethoxypropyl, 3-butoxypropyl, 3-octoxypropyl and 4-methoxybutyl; 3-methoxypropyl and 3-ethoxypropyl are particularly preferred.

Examples of $C_2$–$C_4$alkyl substituted by di-$C_1$–$C_4$alkyl)-amino, preferably dimethylamino or diethylamino, are 3-dimethylaminoethyl, 2-diethyleminoethyl, 3-dimethylaminopropyl, 3-diethylaminopropyl, 3-dibutylaminopropyl and 4-diethylaminobutyl.

Representative examples of $C_3$–$C_{18}$alkyl $R_4$ interrupted by 1, 2 or 3 oxygen atoms are 2-methoxyethyl, 2-ethoxyethyl, 2-butoxyethyl, 2-octoxyethyl, 2-dodecyloxyethyl, 3,6-dioxaoctyl, 3,6-dioxadecyl, 3,6,9-trioxaundecyl and 3,6,9-trioxatridecyl; 3,6-dioxadecyl is preferred.

Representative examples of $C_1$–$C_{18}$alkoxy $R_1$ and $R_7$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy and octoxy, are preferred.

Representative examples of $C_5$–$C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of substituted or unsubstituted $C_5$–$C_{12}$cycloalkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Cyclohexyl is preferred.

Representative examples of $C_3$–$C_6$alkenyl $R_1$ and $R_7$ are allyl, 2-methylallyl, butenyl, pentenyl, and hexenyl. Alkenyls in which the carbon atom in the 1-position is saturated are preferred; allyl is particularly preferred.

Examples of substituted phenyl are methylphenyl, dimethylphenyl, trimethylphenyl, t-butylphenyl and di-t-butylphenyl.

Examples of phenylalkyl unsubstituted or substituted on the phenyl are benzyl, methylbenzyl, dimethylbenzyl, t-butylbenzyl and 2-phenylethyl. Benzyl is preferred.

Acyl $R_1$ and $R_7$ containing up to 8 carbon atoms can be a saturated or unsaturated aliphatic group or an aromatic group. Representative examples are formyl, acetyl, propionyl, butyryl, pentanoyl, hexanoyl, octanoyl, benzoyl, acryloyl and crotonyl. Acetyl is preferred.

If the group

is a 5-membered to 7-membered heterocyclic group, said group is preferably saturated and can optionally contain a further heteroatom, for example nitrogen or oxygen.

Representative examples are 1-pyrrolidyl, 1-piperidyl, 4-morpholinyl, 4-methyl-1-piperazinyl, 1-hexahydroazepinyl, 5,5,7-trimethyl-1-homopiperazinyl and 5,5,5,7-tetramethyl-1-homopiperazinyl; 4-morpholinyl is preferred.

Examples of alkylene containing up to 12 carbon atoms are ethylene, propylene, trimethylene, tetramethylene, pentamethylene, 2,2-dimethyl-trimethylene, hexamethylene, trimethylhexamethylene, decamethylene and dodecamethylene.

Representative examples of $C_4$–$C_{12}$alkylene $R_{11}$ interrupted by 1, 2 or 3 oxygen atoms are 3-oxapentane-1,5-diyl, 4-oxaheptane-1,7-diyl, 4,7-dioxadecane-1,10-diyl, 4,9-dioxadodecane-1,12-diyl, 3,6-dioxaoctane-1,8-diyl and 3,6,9-trioxaundecane-1,11-diyl.

$R_1$ is preferably hydrogen, $C_1$–$C_4$alkyl, OH, $C_4$–$C_{12}$alkoxy, $C_5$–$C_8$cycloalkoxy, allyl, benzyl, acetyl or 2-hydroxyethyl, in particular hydrogen or methyl; $R_2$ is preferably 2,2,6,6-tetramethyl-4-piperidyloxy or 1,2,2,6,6-pentamethyl-4-piperidyloxy.

Those compounds of the formula (I) are preferred in which $R_2$ is a group $-OR_4$, $-SR_4$ or

in which $R_4$ is $C_1$–$C_{12}$alkyl, $C_5$–$C_8$cycloalkyl which is unsubstituted or mono-, di- or tri-substituted by $C_1$–$C_4$alkyl, phenyl, benzyl, $C_3$–$C_{12}$alkyl interrupted by 1 or 2 oxygen atoms, $C_2$–$C_3$alkyl substituted in the 2- or 3-position by di-($C_1$–$C_4$alkyl)-amino, or a group of the formula (II) and $R_5$ and $R_6$ which can be identical or different are hydrogen, $C_1$–$C_{12}$alkyl, $C_5$–$C_8$cycloalkyl which is unsubstituted or mono, di- or tri-substituted by $C_1$–$C_4$alkyl, benzyl, $C_2$–$C_3$alkyl substituted in the 2- or 3-position by $C_1$–$C_4$alkoxy or di-($C_1$–$C_4$alkyl)-amino, or a group of the formula (II), or the group

is 1-pyrrolidyl, 1-piperidyl, 4-morpholinyl, 4-methyl-1-piperazinyl or 1-hexahydro-azepinyl, m is an integer from 2 to 6 and, if m is 2, $R_3$ is one of the groups of the formula (IIIa)–(IIIe) in which $R_8$, $R_{10}$, $R_{12}$ and $R_{14}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, benzyl or a group of the formula (II), $R_9$ is $C_2$–$C_{10}$alkylene, cyclohexylene, cyclohexylenedimethylene, methylenedicyclohexylene, isopropylidenedicyclohexylene or xylylene, $R_{11}$ is as defined for $R_9$ or is $C_4$–$C_{10}$alkylene interrupted by 1 or 2 oxygen atoms, $R_{13}$ is hydrogen or methyl, n is zero of 1 and p is an integer from 2 to 6, and, if m is 3, 4, 5 or 6, $R_3$ is a group of the formula (IV) in which $R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and, if m is 3, $R_3$ can also be a group of the formula (Va) or (Vb) in which $R_{20}$ is $C_2$–$C_6$alkylene and $R_{21}$, $R_{22}$, $R_{23}$ and $R_{24}$ which can be identical or different are as defined for $R_8$, and r and s which can be identical or different are integers from 2 to 6.

Those compounds of the formula (I) are particularly preferred in which $R_2$ is a group —$OR_4$ or

in which $R_4$ is $C_1$–$C_{10}$alkyl, cyclohexyl which is unsubstituted or mono-, di- or tri-substituted by $C_1$–$C_4$alkyl, phenyl, benzyl or a group of the formula (II) and $R_5$ and $R_6$ which can be identical or different are hydrogen, $C_1$–$C_{10}$alkyl, cyclohexyl which is unsubstituted or mono-, di- or tri-substituted by $C_1$–$C_4$alkyl, benzyl, $C_2$–$C_3$alkyl substituted in the 2- or 3-position by methoxy, by ethoxy, by dimethylamino or by diethylamino, or a group of the formula (II), or the group

is 4-morpholinyl, m is an integer from 2 to 6 and, if m is 2, $R_3$ is one of the groups of the formula (IIIa)–(IIIe) in which $R_8$, $R_{10}$, $R_{12}$ and $R_{14}$ which can be identical or different are hydrogen, $C_1$–$C_{10}$alkyl, cyclohexyl which is unsubstituted or mono-, di- or tri-substituted by $C_1$–$C_4$alkyl, benzyl or a group of the formula (II), $R_9$ is $C_2$–$C_8$alkylene, cyclohexylenedimethylene, methylenedicyclohexylene or xylylene, $R_{11}$ is as defined for $R_9$ or is $C_4$–$C_{10}$alkylene interupted by 1 or 2 oxygen atoms, $R_{13}$ is hydrogen or methyl, n is zero or 1 and p is 2 or 3, and, if m is 3, 4, 5 or 6, $R_3$ is a group of the formula (IV) in which $R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and, if m is 3, $R_3$ can also be a group of the formula (Va) or (Vb) in which $R_{20}$ is $C_2$–$C_3$alkylene, $R_{21}$, $R_{22}$, $R_{23}$ and $R_{24}$ which can be identical or different are as defined for $R_8$ and r and s which can be identical or different are integers from 3 to 5.

Those compounds of the formula (I) are of special interest in which $R_2$ is a group —$OR_4$ or

in which $R_4$ is $C_1$–$C_8$alkyl, cyclohexyl, benzyl, $C_2$–$C_3$alkyl substituted in the 2- or 3-position by methoxy, by ethoxy, by dimethylamino or be diethylamino, or a group of the formula (II) or $R_5$ can also be hydrogen, or the group

is 4-morpholinyl, m is 2, 3 or 4 and, if m is 2, $R_3$ is one of the groups of the formula (IIIb)–(IIIe) in which $R_{10}$ and $R_{12}$ which can be identical or different are hydrogen, $C_1$–$C_4$alkyl, cyclohexyl or a group of the formula (II), $R_9$ is $C_2$–$C_6$alkylene, $R_{11}$ is $C_2$–$C_6$alkylene, cyclohexylenedimethylene, methylenedicyclohexylene, xylylene or $C_4$–$C_{10}$alkylene interrupted by 1 or 2 oxygen atoms, $R_{13}$ is hydrogen, n is zero, $R_{14}$ is hydrogen, $C_1$–$C_4$alkyl or cyclohexyl and p is 2 or 3, and, if m is 3 or 4, $R_3$ is a group of the formula (IV) in which $R_{15}$ and $R_{19}$ which can be identical or different are as defined for $R_{10}$, and $R_{16}$, $R_{17}$ and $R_{18}$ which can be identical or different are $C_2$–$C_6$alkylene and q is zero of 1.

Those compounds of the formula (I) are of particular interest in which $R_1$ is hydrogen or methyl, $R_2$ is a group —$OR_4$ or

in which $R_4$ is $C_1$–$C_4$alkyl, 2,2,6,6-tetramethyl-4-piperidyl or 1,2,2,6,6-pentaethyl-4-piperidyl and $R_5$ and $R_6$ which can be identical or different are $C_1$–$C_8$alkyl, 2,2,6,6-tetramethyl-4-piperidyl or 1,2,2,6,6-pentamethyl-4-piperidyl, or $R_5$ is hydrogen, or the group

is 4-morpholinyl, m is 2, 3, or 4, and if m is 2, $R_3$ is one of the groups of the formula (IIIc), (IIId) or (IIIe) in which $R_{10}$ and $R_{12}$ which can be identical or different are hydrogen, methyl, isopropyl, cyclohexyl, 2,2,6,6-tetramethyl-4-piperidyl or 1,2,2,6,6-pentamethyl-4-piperidyl, $R_{11}$ is $C_2$–$C_6$alkylene or $C_6$–$C_{10}$alkylene interrupted by 2 oxygen atoms, $R_{13}$ is hydrogen, n is zero, $R_{14}$ is hydrogen, methyl or cyclohexyl and p is 2, and, if m is 3 or 4, $R_3$ is a group of the formula (IV) in which $R_{15}$ and $R_{19}$ which can be identical or different are as defined for $R_{10}$, and $R_{16}$, $R_{17}$ and $R_{18}$ which can be identical or different are $C_2$–$C_3$alkylene and q is zero of 1.

Those compounds of the formula (I) are also of particular interest in which $R_1$ is hydrogen or methyl, $R_2$ is 2,2,6,6-tetramethyl-4-piperidyloxy or 1,2,2,6,6-pentamethyl-4-piperidyloxy, m is 2, 3 or 4 and, if m is 2, $R_3$ is a group of the formula (IIIc) or (IIIe) in which $R_{10}$ and $R_{12}$ which can be identical or different are hydrogen, cyclohexyl, 2,2,6,6-tetramethyl-4-piperidyl or 1,2,2,6,6-pentamethyl-4-piperidyl, $R_{11}$ is $C_2$–$C_6$alkylene, $R_{14}$ is hydrogen or methyl and p is 2, and, if m is 3 or 4, $R_3$ is a group of the formula (IV) in which $R_{15}$ and $R_{19}$ which can be identical or different are hydrogen, 2,2,6,6-tetramethyl-4-piperidyl or 1,2,2,6,6-pentamethyl-4-piperidyl, $R_{16}$, $R_{17}$ and $R_{18}$ which can be identical or different are $C_2$–$C_3$alkylene and q is zero of 1.

The compounds of the formula (I) can be prepared by processes known per se, for example as described in U.S. Pat. No(s). 3,925,376 and 4,108,829, by reacting, in any order, cyanuric chloride with the compounds of the formula (VIa)–(VIc)

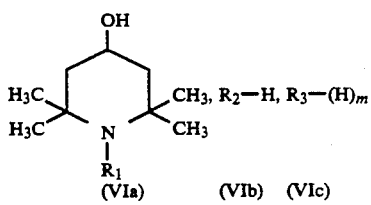

(VIa)   (VIb)   (VIc)

using the appropriate molar ratios, in particular stoichiometric ratios. The reactions are preferably carried out in a solvent such as e.g. toluene, xylene, trimethylbenzene, decalin, dichloromethane, dichloroethane or trichloroethylene, operating at a temperature between e.g. −30° C. and 200° C., preferably −20°0 C. to 150° C. The hydrohalic acid released in the various reactions is neutralized preferably by an inorganic base, for example sodium or potassium hydroxide or carbonate, in a quantity at least equivalent to the acid released.

The reagents of the formula (VIa) can also be used e.g. in the form of sodium or potassium alcoholates. The compounds of the formula (VIa)–(VIc) used for the preparation of the compounds of the formula (I) are commercial products or products which can easily be prepared by known processes.

As mentioned at the outset, the compounds of the formula (I) are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, such as, for example, ethylene/propylene, linear low-density polyethylene (LLDPE) and its mixtures with low-density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidenenorbornene; as well as mixtures of such copolymers and their mixtures with polymers mentioned in 1) above, for example polypropylene/ethylene-propylene copolymers, LDPE/EVA, LDPE/EAA, LLDPE/EVA and LLDPE/EAA.

3a. Statistical or alternating copolymers of α-olefins with carbon monoxide.

3b. Hydrocarbon resins (for example $C_5$–$C_9$) and hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, such as, for example, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS, MBS, ASA or AES polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example polyvinyl chloride, polyvinylidene chloride, polyvinyl fluoride, polyvinyl fluoride, polyvinylidene fluoride, as well as copolymers thereof, as for example vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and polyoxymethylenes which contain ethylene oxide as a comonomer; polyacetals modified with thermoplastic polyurethanes, acrylates of MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one hand and on the other hand aliphatic or aromatic polyisocyanates, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6/6, polyamide 6/10, 6/9, 6/12 and 4/6, polyamide 11, polyamide 12, aromatic polyamides obtained by condensation of m-xylenediamine and adipic acid; polyamides prepared from hexamethylenediamine and isophthalic and/or tetraphthalic acid and optionally an elastomer as modifier, for example poly-2,4,4-trimethyl-hexamethylene-terephthalamide or poly-m-phenylene-isophthalamide. Further, copolymers of the aforementioned polyamides with polyolefins, olefin copolymers, ionomers or chemically bonded or grafted elastomers; or with polyethers, such as, for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-[2,2-(4-hydroxyphenyl)-propane] terephthalate and polyhydroxybenzoate as well as block copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as cross-linking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or cellulose ethers, such as methylcellulose; rosins and their derivatives.

27. Mixtures of polymers as mentioned above, for example PP/EPDM, polyamide 6/EPDM or ABS, PVC/EVA, PVC/ABS, PVC/MBS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6/6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or timellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubbers, for example natural latex or latexes of carboxylated sytrene/butadiene copolymers.

The compound of the formula (I) are particularly suitable for improving the light stability, heat stability and oxidation stability of polyolefins, especially polyethylene and polypropylene. The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably from 0.05 to 1%.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

In general, the compounds of the formula (I) can be added to the polymeric materials before, during or after the polymerization or cross-linking of said materials.

The materials stabilized with the products of the formula (I) can be used for the production of mouldings, films, tapes, monofilaments, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in a mixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethylphenol, 2,6-diocatedecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'thiobis(4- octylphenol), 4,4'thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(4,6-di-tert-butylphenol), 2,2'-ethylidenebis-(4,6-di-tert-butylphenol), 2,2'-ethylidenebis(6-tert-butyl-4-isobutylphenol), 2,2'-methylenebis[6-(α-methylbenzyl)-4-nonylphenol], 4,4'-methylenebis(2,6-di-tert-butylphenol), 4,4'-methylenebis-(6-tert-butyl-2-methylphenol, 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)-butyrate], bis(3-tertbutyl-4-hydroxy-5-methylphenyl)-dichlopentadiene, bis[2-(3'-tert-butyl-2'-hydroxy-5'-methylbenzyl)-6-tert-butyl-4-methylphenyl] terepthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris-(4-tert-butyl-3-hydroxy-2,6-dimethylbenzyl) isocyanurate, di-octadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6 Acylaminophenols, for example lauric acid 4-hydroxyanilide, stearic acid 4-hydroxyanilide, 2,4-bis-(octylmercapto)-6-(3,5-di-tert-butyl-4-hydroxyanilnio)-s-triaxine, octyl N-(3,5-di-tert-butyl-4-hydroxyphenyl)-carbamate.

1.7. Esters of b-(3,5-di-tert-butyl-4-hydroxyphenyl)-propionic acid with mono- or poly-hydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)-hydrazine.

2. UV absorbers and light stabilizers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy-3',5'-di-tert-amyl and 3',5'-bis-(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoylresorcinol, bis(4-tert-butyl-benzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-di-phenylacrylate, methyl α-carbomethoxycinnamate, methyl α-cyano-β-methyl-p-methoxycinnamate, butyl α-cyano-β-methyl-p-methoxycynnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6 Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl) 1,2,3,4-butaneteracarboxylate, 1,1'-(1,2-ethanediyl)bis-(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixtures with 2-ethoxy-2'-ethyl-5,4'-di-tert-butyloxanilide and mixtures of ortho- and paramethoxy-disubstituted oxanilides and mixtures of o- and p-ethoxydisubstituted oxanilides.

2.8 2-(2-Hydroxyphenyl)-1,3,5-triazines, for example 2,4,5-tris(2-hydroxy-4-oxtyloxy-phenyl)-1,3,5-triazine, 2,-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalic acid diamide, N-salicylal-N'-salicyloylhydraxine, N,N'-bis(salicyloyl)hydraxine, N,N'-bis(3,5-di-tert-butyl-4-hydroxyphenylpropionyl)hydrozine, 3-salicyloyl-amino-1,2,4-triazone, bis(benzylidene)oxalodihydrazide.

4. Phosphites and phosphonites, for example triphenyl phosphite, diphenyl aklyl phosphites, phenyl dialkyl phosphites, tris(nonylphenyl) phosphite, trialuryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4′-bi-phenylenediphosphonite, 3,9-bis(2,4-di-tert-butylphenoxy)-2,4,8,10-tetraoxa-3,9-di-phosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilizers, for example copper salts in combination with iodides and/or phosphorus compounds and salts of divalent manganese.

7. Basic co-stabilizers, for example malamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate and K palmitate, antimony pyrocatecholate or zinc pyrocatecholate.

8. Nucleating agents, for example 4-tert-butyl-benzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxides, carbon black, graphite.

10. Other additives, for example plasticizers, lubricants, emulsifiers, pigments, optical brighteners, flameproofing agents, antistatic agents and blowing agents.

The compounds of the invention can also be used as stabilisers, especially as light stabilisers, for almost all materials known in the art of photographic reproduction.

By way of example, attention is drawn to the great number of materials which find utility in systems that are based on the light-, heat- or pressure-induced reaction of a colour former (electron donor) with a colour developer (electron acceptor). Exemplary of such colour formers are triarylamines such as 3,3-bis(p-dimethylaminophenyl)-5-dimethylaminophthalides[CVL], 3,3-bis-(p-dimethylamino)phthalides, 3-(p-dimethylaminophenyl)-3-1,3-dimethylindole-3-yl)phthalides and 3-(p-dimethylaminophenyl)-3-(2-methylindole-3-yl)phthalides, xanthenes such as rhodamine-B-anilinolactam, rhodamine-(p-nitroanilino)lactam, rhodamine-B(p-chloranilino)lactam, 2-dibenzylamino-6-diethyleminofluorane, 2-anilino-6-diethylaminofluoran, 2-anilino-3-methyl-6-diethylaminofluoran, 2-anilino-3-methyl-6-(N-cyclohexyl-N-methyl)aminofluoran, 2-o-chloroanilino-6-diethylaminofluoran, 2-o-chloroanilino-6-dibutylaminofluoran, 2-p-chloroanilino-6-diethylaminofluoran, 2-octylamino-6-diethylaminofluoran, 2-p-acetylanilino-6-diethylaminofluoran, 2-ethoxyethylamino-3-chloro-6-diethylaminofluoran, 2-anilino-3-chloro-6-diethylaminofluoran, 2-diphenylamino-6-diethylaminofluoran, 2-anilino-3-methyl-6-(N-ethyl-N-isoamyl)aminofluoran, 2-anilino-3-methyl-6di-phenylaminofluoran, 2-anilino-6-(N-ethyl-N-tolyl)aminofluoran, 2--anilino-3-methoxy-6-dibutylaminofluoran, 2-anilino-3-methyl-6-di-n-butylaminofluoran, 2-anilino-3-methyl-6-(N-tetrahydrofurfuryl)aminofluoran as well as 2-anilino-3-methyl-6-(N-n-butyl-N-tetrahydrofurfuryl)aminofluoran, thiazines such as benzoyl leuco methylene blue and p-nitrobenzyl leuco methylene blue, oxazines such as 3,7-bis(diethylamino)-10-benzoylphenoxazine and 3,7-bis(diethylamino)-10-acetylphenoxazine, and spiro compounds such as 3-methylspiro-dinaphthopyran, 3-benzyl-spiro-dinaphthopyran and 3-propyl-spiro-dibenzopyran.

Illustrative examples of suitable colour developers are: salicyclic acid and salicyclic acid derivatives as well as corresponding zinc salts such as zinc salicylate, phenolic resins which may also contain zinc, acid-activated clay, 4,4′-isopropylidenediphenols, 2,2′-methylenebisphenols, bisphenol A and derivatives, 4-hydroxydiphthalates, monophthalates, bis(hydroxyphenyl)sulfides, 4-hydroxyphenylarylsulfones and -sulfonates, 1,3-bis[2-(hydroxyphenyl)-2-propyl]benzenes, benzyl-4-hydroxyphenylacetate, 4-hydroxybenzoyloxybenzoates, bisphenolsulfones, 4-hydroxyphenylacetate, butylphenol, 4-phenylphenol, α- and β-naphthol, thymol, catechin, pyrogallol, hydroquinone, resorcinol, alkyl-p-hydroxybenzoates, benzoic acid, oxalic acid, maleic acid, citric acid succinic acid, stearic acid boric acid and derivatives of thiourea.

If the recording material is a heat-sensitive paper, the compounds of the invention are typically applied to the substrate, or in a separate protective layer, as a dispersion together with dispersions of the colour developer and the colour former.

If the recording material is a pressure-sensitive paper, the compounds of the invention can be present in the donor layer as well as in the receiver sheet or in both.

Materials for the Cyclor ® process can also be protected by the compounds of this invention. In this process, the compounds present in the receiver sheet stabilise the dyes and prevent the colour developer from yellowing on exposure to light.

The compounds of the invention can be successfully used in materials for the heat diffusion dye transfer process and for the thermowax transfer process.

The compounds of the invention have further utilities in thermographic processes, in which single colour or multicolour patterns can be produced by spot heating. In such processes, a reaction can be initiated either direct by heating, as is frequently the case, for example, when using recording papers, or produced within a conductive layer by an electric current which results from contact with an electrode which may have the form of a character. Further thermographic processes utilise two layers which, during the application of heat, are in contact with each other or are at least in very close proximity. In this method, a dye or a dye precursor, or a dispersion of a dye or pigment, in a low-melting medium is transferred from the donor layer to the receiver layer by diffusion, sublimation or capillary action. Of particular importance here is the dye diffusion process, in which disperse dyes are transferred from a layer of, for example, polyvinyl butyral or cellulose derivative to a layer of polyester or polycarbonate. The donor sheet is normally coated on the back with a layer of high-melting, heat-stable polymer, for example polysulfone, and a dye-containing layer of a softer binder in which the dye should preferably be soluble. Physical treatments are ordinarily carried out to reduce static charge. The receiver materials consist of preferably a white support (paper or plastics material) to which is applied a layer of polyester or polycarbonate, or also of PVC, PVA or polymer mixtures. This layer may additionally contain plasticisers so as to obtain a softening point in the advantageous range from 50° to 150° C. Surfactants and/or solid particles serve the purpose of facilitating the separation of donor sheet and receiver sheet after the transfer process.

Thermoelements or electromagnetic radiation such as infrared or laser light, which must be directed on to the area to be heated, act as heat source. The method of control and the nature of the heat source determine to a very great extent the quality, especially the resolution and gradation, of the image.

Further, the compounds of the invention are also suitable for protecting materials for processes in which the image formation is effected with toners. These are materials in which, in one layer, a certain tackiness is produced or eliminated by means of electrostatic, electrophoretic or magnetographic processes, as well as by photopolymerisation or photoplastification processes. In this case, the compounds of the invention are present in the toner, which may be in liquid or powder form, together with the other customary components such as polymer, dye, and viscosity-determining substances. Mention may also be made of materials in which an image is produced by photooxidation of dyes. These materials too can be protected by the compounds of the invention.

The compounds of the invention can also be successfully used in the printing inks employed in letterpress, lithographic, rotogravure and screen printing. The compounds are particularly suitable for use in inks, for example in writing inks for fountain pens, ballpoint pens, felt-tip pens, ink pads and typewriter ribbons. Particular importance attaches to their use in inks for the ink jet printing process and also in recording materials suitable therefor.

Inks for the ink jet printing process are normally classified in three groups: aqueous inks, and inks based on organic solvents and on waxes.

Solvents for the second group may be alcohols such as ethanol or ketones such as methyl ethyl ketone, without or in combination with film formers such as nitrocellulose, cellulose acetate phthalate, cellulose acetate butyrate, or acrylate, polyamide, alkyd, epoxy, polyurethane, melamine and polyester resins. Suitable dyes for these inks are, for example, the compounds listed in the Colour Index under "Solvent Dyes" or "Disperse Dyes".

These dyes are also good dyes for the wax-based inks. They are dissolved in a wax which is solid at room temperature and which should dissolve at ca. 60° C. Illustrative of such waxes are carnauba wax and waxes derived from aliphatic esters and amides.

Aqueous inks may contain organic solvents such as glycerol, glycol, diethylene glycol, polyethylene glycol, N-methylpyrrolidone and N-methylimidazolidone, as well as dyes which are listed in the Colour Index under "Direct Dyes" and "Acid Dyes", and also biocides and corrosion inhibitors as well as salts to increase the conductivity. This is important in ink jet processes with electrostatic deflection.

Recording materials for the ink jet printing process may consist of an ordinary paper or a layered material in which a receptor layer for the ink is applied to a paper support or to a support made from a transparent plastics material, for example from polyester or cellulose triacetate.

For paper supports, such receptor layers normally contain fillers such as silica and, if desired, mordants such as polymers or surface-active substances which carry ammonium groups. Illustrative of suitable binders for these receptor layers are gelatin, polyvinyl alcohol and starch derivatives, and homo- or copolymers of vinyl pyrrolidone, (meth)acrylic acid and acrylamide, and also mixtures of these compounds.

If supports made from transparent plastics materials are used, then fillers in the receptor layer will normally be dispensed with.

The compounds of the invention have a special utility as stabilisers in silver halide photographic materials. They can be used in principle in all possible layers of such materials. Stabilisers having a strong absorption between 300 and 400 nm are preferably incorporated above light-sensitive layers and also interlayers, reverse layers and cyan layers. The silver halide materials can be colour materials, for example those for transfer processes, for the silver bleach process and, in particular, for the chromogenic development.

Compounds of the invention, which do not show the strong absorption between 300 and 400 nm, are preferably added to one, two, or all three colour-sensitive layers of chromogenic materials. The sensitised silver halide and the respective dye coupler are present in the layers. Moreover, the layers may contain further stabilisers and/or other modifiers conventionally used in photographic materials.

The yellow couplers are preferably compounds of formula A

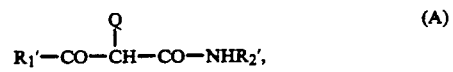

wherein $R_1'$ is alkyl or aryl, $R_2'$ is aryl and Q is hydrogen or a group which can be eliminated by reaction with the oxidised developer.

Another group of yellow couplers comprises those of formula B

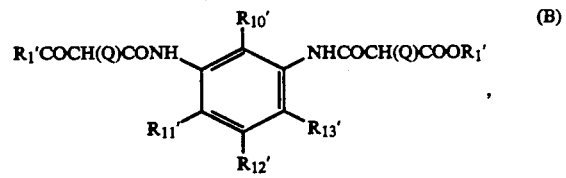

wherein $R_{10}'$ is hydrogen, halogen or alkoxy, $R_{11}'$, $R_{12}'$ and $R_{13}'$ are hydrogen, halogen, alkyl, alkenyl, alkoxy, aryl, carboxyl, alkoxycarbonyl, a carbamoyl group, a sulfone group, a sulfamoyl group, a sulfonamido group, an acylamino group, a ureido group or an amino group, and $R_1'$ and Q are as defined above.

Preferable compounds of formula B are those compounds in which $R_1'$ is tert-butyl, $R_{10}'$ is chloro, $R_{11}'$ and $R_{13}'$ are hydrogen and $R_{12}'$ is alkoxycarbonyl.

Typical examples of customary yellow couplers are the compounds of the following formulae:

(A1)

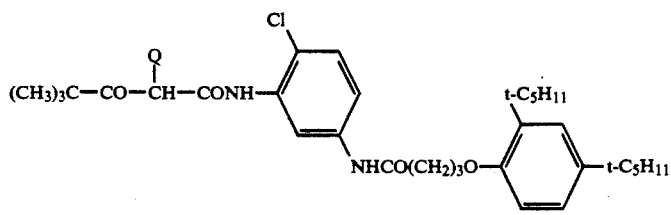

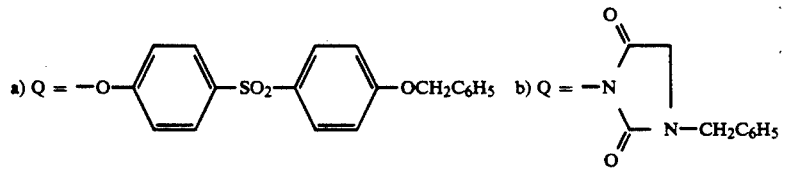

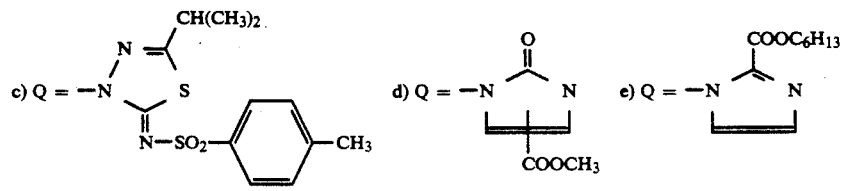

(A2)

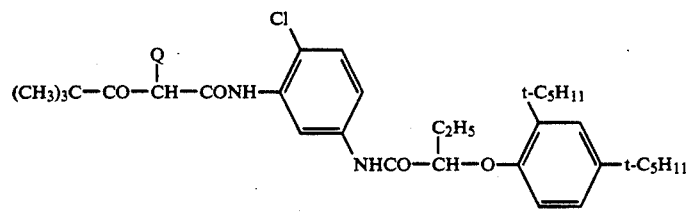

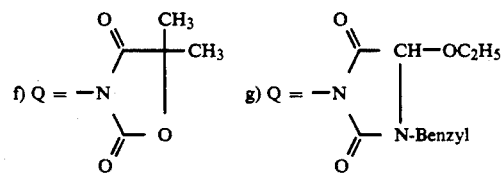

(B1)

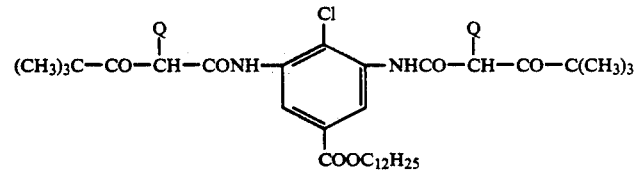

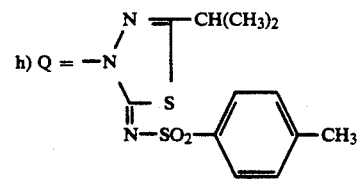

Further examples of yellow couplers will be found in U.S. Pat. No(s). 2,407,210, 2,778,658, 2,875,057, 2,908,513, 2,908,573, 3,227,155, 3,227,550, 2,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, 4,022,620, in DE-A No(s). 1,547,868, 2,057,941, 2,162,899, 2,163,813, 2,213,461, 2,219,917, 2,261,361, 2,261,362, 2,263,875, 2,329,587, 2,414,006, 2,422,812 and in GB patent specifications No(s). 1 425 020 and 1,077,874.

Magenta couplers may typically be simple 1-aryl-5-pyrazolones or pyrazole derivatives which are fused with 5-membered hetero rings, for example imidazopyrazole, pyrazolotriazole or pyrazolotetrazole.

A group of magenta couplers comprises the 5-pyrazolones of formula C

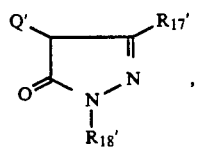

(C)

disclosed in British patent specification 2 003 472. In the above formula C, $R_{17}'$ is hydrogen, alkyl, aryl, alkenyl or a heterocyclic group. $R_{18}'$ is hydrogen, alkyl, aryl, a heterocyclic group, an ester group, an alkoxy group, an alkylthio group, a carboxyl group, an arylamino group, an acylamino group, a (thio)urea group, a (thio)carbamoylgroup, a guanidino group or a sulfonamido group. Q' is a leaving group.

Typical examples of this type of magenta coupler are compounds of formula $C_1$

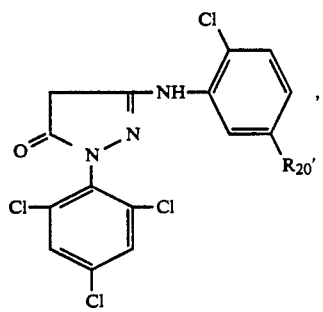

(C$_1$)

wherein $R_{20}'$ is hydrogen, alkyl, acylamino, carbamoyl, sulfamoyl, sulfonamido, alkoxycarbonyl, acyloxy or a urethane group.

Further examples of such four-equivalent magenta couplers will be found in U.S. Pat. No(s). 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866, 3,933,500.

If Q' in formula C is not hydrogen, but a group which is eliminated in the reaction with the oxidised developer, then the magenta couplers are the two-equivalent magenta couplers which are disclosed, for example, in U.S. Pat. No(s). 3,006,579, 3,419,391, 3,311,476, 3,432,521, 3,214,437, 4,032,346, 3,701,782, 4,351,897, 3,227,554, in EP-A-133 503, DE-A-2 944 601, JP-A-78/34 044,74/53 435, 74/53 436, 75/53 372 and 75/122 935.

2-Pyrazolone rings may be linked through a divalent Q' to give in this case so-called bis-couplers. Such couplers are disclosed, for example, in U.S. Pat. No(s). 2,632,702 and 2,618,864, in GB patent specifications 968 461 and 786 859, in JP-A-76/37 646, 59/4086, 69/16 110, 69/26 589, 74/37 854 and 74/29 638. Preferably Y is a O-alkoxyarylthio group.

Further types of magenta couplers are those of the general formulae $D_1$, $D_2$ and $D_3$

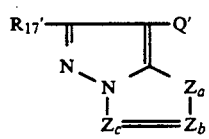

(D$_1$)

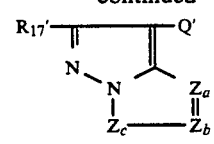

(D$_2$)

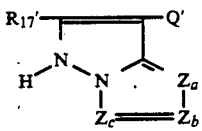

(D$_3$)

wherein $Z_1$, $Z_b$ and $Z_c$ complete a 5-membered ring which may contain 2 to 4 nitrogen atoms. The compounds may accordingly be pyrazoloimidazoles, pyrazolopyrazoles, pyrazolotriazoles or pyrazolotetrazoles. $R_{17}'$ and Q' are as defined for formula C.

Pyrazolotetrazoles are disclosed in JP-A-85/33 552; pyrazolopyrazoles in JP-A-85/43 695; pyrazoloimidazoles in JP-A-85/35 732, JP-A-86/18 949 and U.S. Pat. No. 4,500,630; pyrazolotriazoles in JP-A-85/186 567, JP-A-86/47 957, JP-A-85/215 687, JP-A-85/197 688, JP-A-85/172 982, EP-A-119 860, EP-A-173 256, EP-A-178 789, EP-A-178/788 and in Research Disclosure 84/24,624.

Further pyrazoloazole magenta couplers are disclosed in: JP-A-86/26 947, JP-A-85/140 241, JP-A-85/262 160, JP-A-85/213 937, EP-A-177 765, EP-A-176 804, EP-A-170 164, EP-A-164 130, EP-A-178 794, DE-A-3 516 996, DE-A-3 508 766 and Research Disclosure 81/20919, 84/24531 und 85/25758.

Cyan couplers may typically be derivatives of phenol, of 1-naphthol or of pyrazoloquinazolone. Preferred cyan couplers are those of formula E (E)

$$R_{21}' \text{—} \underset{R_{22}'}{\overset{OH}{\bigcirc}} \text{—} R_{23}'$$

wherein $R_{21}'$, $R_{22}'$, $R_{23}'$ and $R_{24}'$ are hydrogen, halogen, alkyl, carbamoyl, amido, sulfonamido, phosphoramido or ureido. $R_{21}'$ is preferably H or Cl, $R_{22}'$ is preferably an alkyl or amido group. $R_{23}'$ is preferably an amido or ureido group and $R_{24}'$ is preferably hydrogen. Q'' is hydrogen or a leaving group which is eliminated in the reaction with the oxidised developer. A detailed list of cyan couplers will be found in U.S. Pat. No. 4,456,681.

Illustrative examples of customary cyan couplers are:

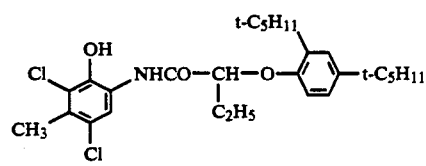

-continued

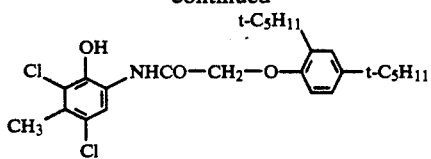

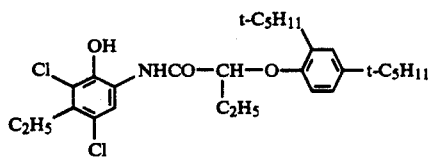

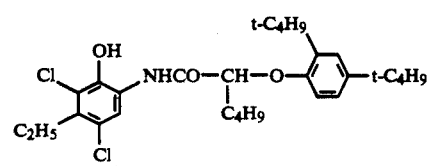

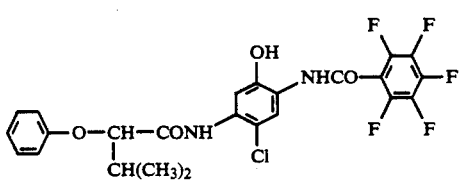

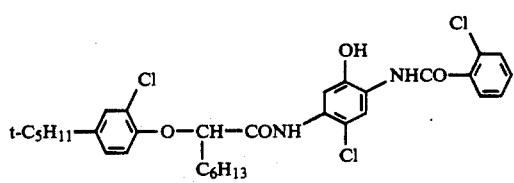

A further class of cyan couplers comprises those of the type of formula F

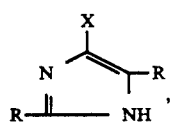
(F)

wherein X is a leaving group and R is a substituent, disclosed, for example, in EP-A-249 453, EP-A-304 856 and EP-A-320 778 and also JP-A-1158 442, of the type of formula G,

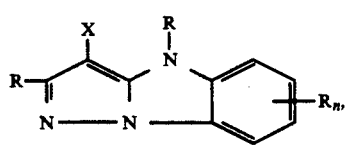
(G)

wherein X is a leaving group and R (identical or different) is a substituent, and n is 0 to 4, disclosed, for example, in EP-A-287 265, JP-A-1 026 853 and JP-A-63 281 161, of the type of formula H,

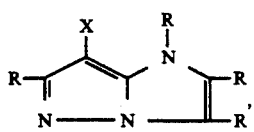
(H)

-continued wherein X is a leaving group and R (identical or different) is a substituent, disclosed, for example, in EP-A-269 436 and JP-A-1028 638, and of the type of formulae I to M

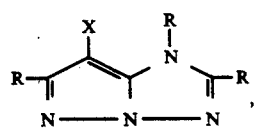
(I)

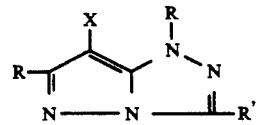
(J)

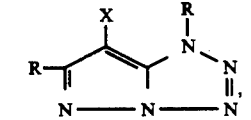
(K)

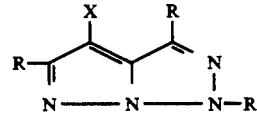
(L)

and

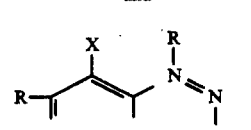
(M)

wherein X is a leaving group and R (identical or different) is a substituent, disclosed, for example, in EP-A-269 436 and EP-A-287 265.

Further examples of cyan couplers will be found in the following U.S. Pat. No(s). 2,369,929, 2,423,730, 2,434,272, 2,474,293, 2,521,908, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,391, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,829,044, 3,880,661, 4,004,929, 4,124,396, 4,333,999, 4,463,086, 4,456,681.

Finally couplers of the types of formulae N to Q may be mentioned

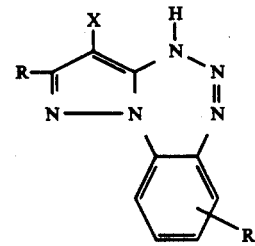
(N)

wherein X is a leaving group and R (identical or different) is a substituent, disclosed, for example, in JP-A-1 003 658,

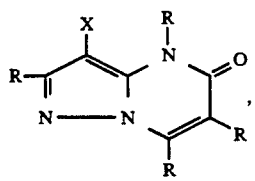
(O)

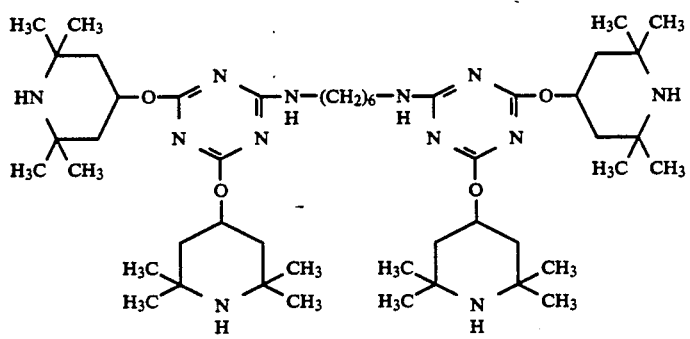

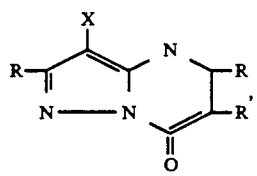

and

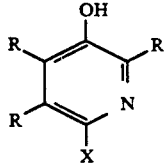
(Q)

wherein X is a leaving group and R (identical or different) is a substituent, disclosed, for example, in EP-A-304 001.

The stabilisers of this invention can also be used in silver halide materials where dyes diffuse in the course of the development from one layer into another, as occurs, for example, in the formation of instant images. Such materials are developed either by treatment with an aqueous composition or purely thermally, in which case the dyes are generated from their precursors only at the exposed areas and are able to diffuse into the receiver layer. In these systems, the silver may also be in the form of an organic salt such as silver behenate or silver sebacate. The stabilisers are preferably incorporated in the receiver layer.

The stabilisers of this invention may be incorporated by themselves or together with the dye coupler and other optional components into the colour photographic material by predissolving them in a high-boiling organic solvent. It is preferred to use a solvent that boils at a temperature higher than 160° C. Typical examples of such solvents are the esters of phthalic acid, phosphoric acid, citric acid, benzoic acid or of fatty acids, as well as epoxides, alkylamides and phenols.

In order to illustrate the present invention more clearly, several examples of the preparation of compounds of the formula (I) are described below; these examples are given by way of illustration only and do not imply any restriction. The compounds disclosed in Examples 4, 5, 6, 10 and 12 correspond to a particular preferred embodiment of the present invention.

EXAMPLE 1

Preparation of the compound 5.06 g (0.22 mol) of metallic sodium are added slowly to a solution of 34.64 g (0.22 mol) of 2,2,6,6-tetramethyl-4-piperidinol in 200 ml of xylene, and the mixture is heated under reflux for 16 hours until the reaction is complete.

The solution thus obtained is added in the course of 2 hours to a solution maintained at −20° C. and containing 20.28 g (0.11 mol) of cyanuric chloride and 180 ml of anhydrous xylene. After the end of the addition, stirring is continued for one hour and then for a further 6 hours at ambient temperature. 5.81 g (0.05 mol) of 1,6-diaminohexane and 8.00 g (0.20 mol) of sodium hydroxide are added, and the mixture thus obtained is heated for 12 hours, the water of reaction being separated off. After the inorganic products have been filtered off while hot, a precipitate is obtained by cooling of the filtrate, and this is separated off and washed with xylene and then with warm isopropanol.

The product thus obtained has a melting point of 247°–249° C.

Analysis for $C_{48}H_{86}N_{12}O_4$; Calculated: C=64.40%; H=9.68%; N=18.77%; Found: C=64.14%; H=9.62%; N=18.62%.

EXAMPLES 2-9

Following the procedure described in Example 1, but using the appropriate reagents in the appropriate molar ratios, the following products of the formula

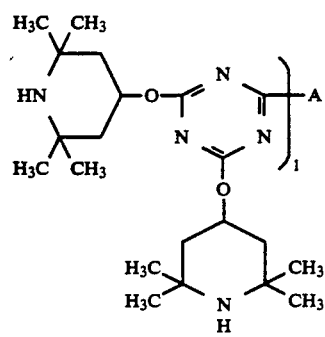

are obtained:

| Example | l | A | m.p. (°C.) |
|---|---|---|---|
| 2 | 2 | —NH—(CH₂)₃—NH— | 222–224 |
| 3 | 2 | 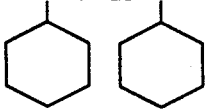 | 263–265 |
| 4 | 2 | 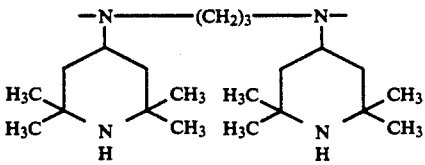 | 178–179 |
| 5 | 2 | 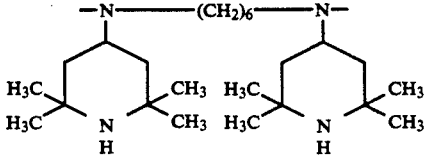 | 236–237 |
| 6 | 2 | 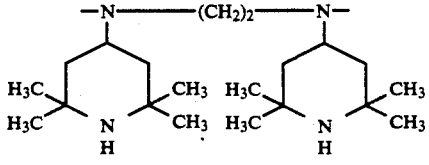 | >300 |
| 7 | 3 | 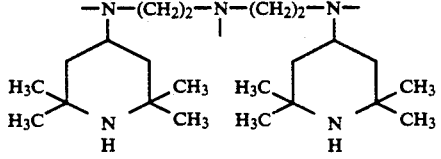 | 134–135 |
| 8 | 3 | —NH—(CH₂)₂—N—(CH₂)₂—NH— | 132–133 |
| 9 | 4 | —NH—(CH₂)₃—N—(CH₂)₂—N—(CH₂)₃—NH— | 244–245 |

EXAMPLE 10

Preparation of the compound

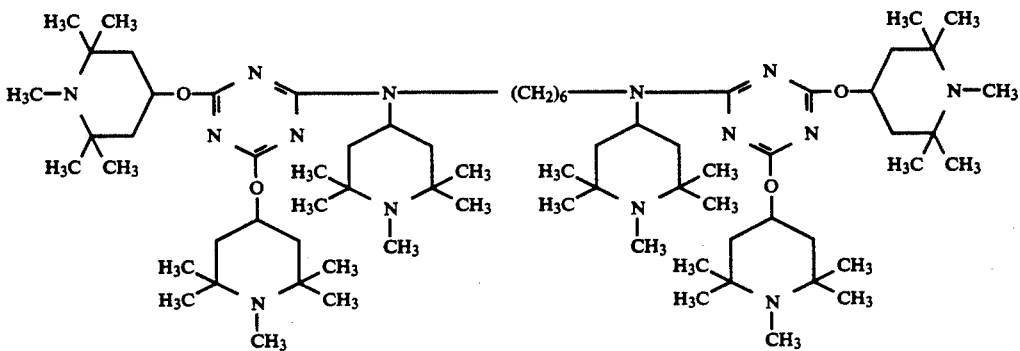

A mixture consisting of 13.81 g (0.30 mol) of formic acid and a solution obtained by dissolving 9.64 g (0.32 mol) of paraformaldehyde in 30 ml of an aqueous 2% sodium hydroxide solution is added slowly in 2 hours to a solution, heated to 115° C., containing 52.74 g (0.045 mol) of the produce from Example 5 in 100 ml of xylene; during the addition, the water added and that of reaction are simultaneously removed azeotropically. The produce is cooled to 60° C., a solution of 16 g (0.40 mol) of sodium hydroxide in 80 ml of water is added and the mixture is heated at 60° C. for 1 hour.

After the aqueous phase has been separated off, the mixture is dehydrated by separating off the water azeotropically and subsequently evaporated, leaving a product of melting point 202°–203° C.

Analysis for $C_{72}H_{132}N_{14}O_4$; Calculated: C=68.75%; H=10.58%; N=15.59%;

Found: C=68.40%; H=10.49%; N=15.45%.

EXAMPLE 11

Following a procedure analogous to that described in Example 10, but using the product from Example 7, the compound

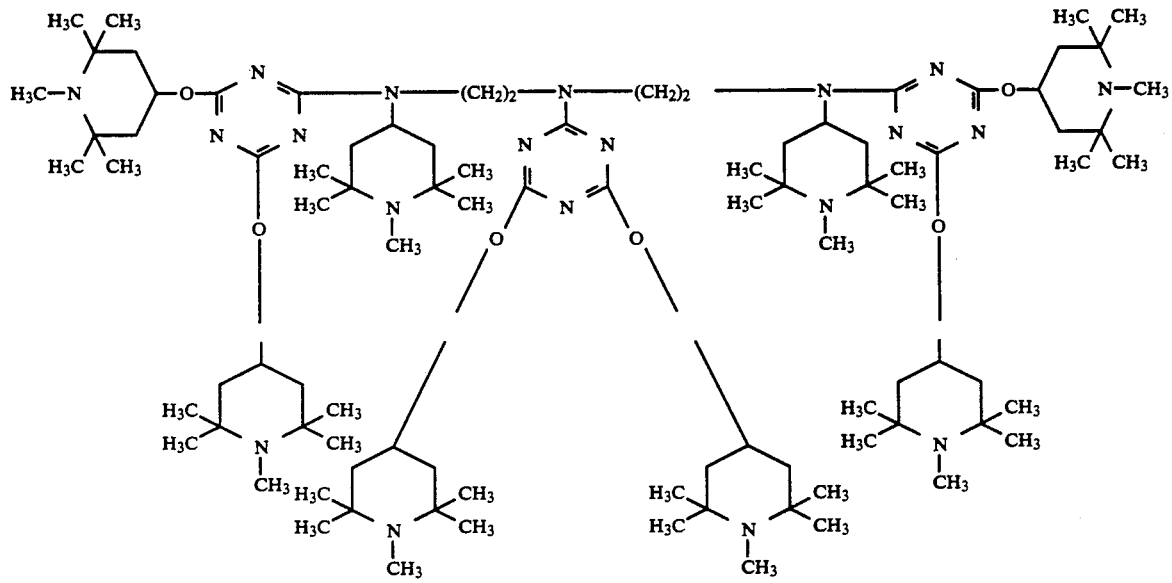

of melting point 162°–164° C. is obtained.

EXAMPLE 12

Preparation of the product

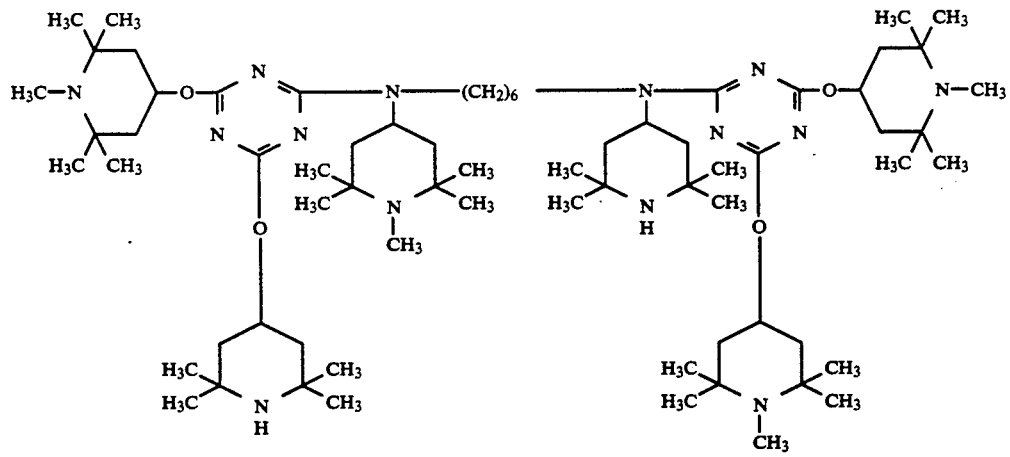

A) Preparation of N,N'-bis(4,6-dichloro-1,3,5-triazin-2-yl)-N,N'-bis(2,2,6,6-tetramethyl-4-piperidyl)-1,6-diaminohexane.

A solution of 118.20 g (0.30 mol) of N,N'-bis(2,2,6,6-tetramethyl-4-piperidyl)-1,6-di-aminohexane in 150 ml of 1,2-dichloroethane is added slowly in the course of 2 hours to a solution, maintained at 0° C., containing 110.70 g (0.60 mol) of cyanuric chloride in 800 ml of 1,2-dichloroethane. 250 ml of an aqueous solution containing 25.20 g (0.63 mol) of sodium hydroxide are then added in 30 minutes at 0° C., and stirring is continued for 2 hours at 0° C. The aqueous phase is then separated off, the organic phase is washed repeatedly with water and dehydrated by means of anhydrous sodium sulfate, and a white solid of melting point 161°–163° C. is precipitated by evaporation of the solvent.

B) A mixture containing 10 g (0.014 mol) of N,N'-bis(4,6-dichloro-1,3,5-triazin-2-yl)-N,N'-bis(2,2,6,6-tretramethyl-4-piperidyl)-1,6-diamino-hexane, 9.90 g (0.058 mol) of 1,2,2,6,6-pentamethyl-4-piperidinol, 4.60 g (0.11 mol) of sodium hydroxide powder and 60 ml of xylene is heated for 8 hours at 80° C. After completion of the reaction, the mixture is repeatedly washed with water at ambient temperature, the aqueous phase is separated off and the organic solution is dehydrated by means of anhydrous sodium sulfate; evaporation of the solvent gives a solid which is crystallized from a 1:1 ethanol/methanol mixture.

A product of melting point 227°–229° C. is obtained in this way.

Analysis for $C_{68}H_{128}N_{14}O_4$; Calculated: $C=68.36\%$; $H=10.49\%$; $N=15.94\%$; Found: $C=67.86\%$; $H=10.41\%$; $N=15.83\%$.

EXAMPLE 13

(Antioxidant action in polypropylene plaques): 1 g of each of the compounds indicated in Table 1 and 1 g of calcium stearate are mixed in a slow mixer with 1000 g of polypropylene powder of melt index=2 g/10 min (measured at 230° C. and 2.16 kg).

The mixtures are extruded twice at 200°-220° C. to give polymer granules which are then converted into plaques of 1 mm thickness by compression-moulding at 230° C. for 6 minutes.

The plaques are then punched using a DIN 53451 mould, and the specimens obtained are exposed in a forced-circulation air oven maintained at a temperature of 135° C.

The specimens are checked at regular intervals by folding them by 180° C. in order to determine the time (in hours) required for fracturing them. The results obtained are given in Table 1.

TABLE 1

| Stabilizer | Time to fracture (hours) |
| --- | --- |
| without stabilizer | 250 |
| compound from Example 4 | 1130 |
| compound from Example 5 | 1200 |
| compound from Example 6 | 1140 |
| compound from Example 10 | 1340 |
| compound from Example 11 | 1130 |

EXAMPLE 14

(Light-stabilizing action in polypropylene tapes): 1 g of the compound indicated in Table 2, 0.5 g of tris(2,4-di-t-butyl-phenyl) phosphite, 0.5 g of pentaerithritol tetrakis-3-(3,5-di-t-butyl-4-hydroxyphenyl)propionate and 1 g of calcium stearate are mixed in a slow mixer with 1000 g of polypropylene powder of melt index=2 g/10 min (measured at 230° C. and 2.16 kg).

The mixtures are extruded at 200°-220° C. to give polymer granules which are then converted into stretched tapes of 50 mm thickness and 2.5 mm width, using a pilot-type apparatus (Leonard-Sumarigo(VA) Italy) and operating under the following conditions:

| | |
| --- | --- |
| extruder temperature = | 210-230° C. |
| head temperature = | 240-260° C. |
| stretch ratio = | 1:6 |

The tapes thus prepared are exposed, mounted on a white card, in a Weather-O-Meter 65 WR (ASTM G26-77) with a black panel temperature of 63° C.

The residual tenacity is measured on samples, taken after various times of exposure to light by means of a constant-speed tensometer; the exposure time (in hours) needed to halve the initial tenacity ($T_{50}$) is then calculated. Tapes prepared under the same conditions as indicated above, but without addition of stabilizer, are exposed for comparison.

The results obtained are shown in Table 2:

TABLE 2

| Stabilizer | $T_{50}$ (hours) |
| --- | --- |
| without stabilizer | 500 |
| compound from Example 4 | 2730 |
| compound from Example 5 | 2530 |

TABLE 2-continued

| Stabilizer | $T_{50}$ (hours) |
| --- | --- |
| compound from Example 7 | 2840 |
| compound from Example 11 | 2500 |
| compound from Example 12 | 2720 |

What is claimed is:

1. A stabilized composition which comprises
(a) an organic material susceptible to degradation induced by light, heat or oxidation, and
(b) an effective stabilizing amount of a compound of formula I

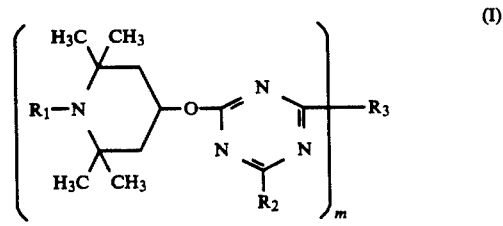

in which $R_1$ is hydrogen, $C_1-C_8$alkyl, O°, OH, NO, $CH_2CN$, $C_1-C_{18}$alkoxy, $C_5-C_{12}$cycloalkoxy, $C_3-C_6$alkenyl, $C_7-C_9$phenylalkyl which is unsubstituted or mono-, di- or tri-substituted on the phenyl by $C_1-C_4$alkyl, $C_1-C_8$acyl or $C_2-C_4$alkyl substituted by OH in the 2-, 3- or 4-position, $R_2$ is a group $-OR_4$, $-SR_4$ or

wherein $R_4$ is $C_1-C_{18}$alkyl, $C_5-C_{12}$cycloalkyl which is unsubstituted or mono-, di- or tri-substituted by $C_1-C_4$alkyl, phenyl which is unsubstituted or mono-, di- or tri-substituted by $C_1-C_4$alkyl, $C_7-C_9$phenylalkyl which is unsubstituted or mono-, di or tri-substituted on the phenyl by $C_1-C_{18}$alkyl, $C_3-C_{18}$alkyl interrupted by 1, 2 or 3 oxygen atoms, $C_2-C_4$alkyl substituted in the 2-, 3- or 4-position by di-($C_1-C_4$alkyl)-amino, or a group of the formula (II)

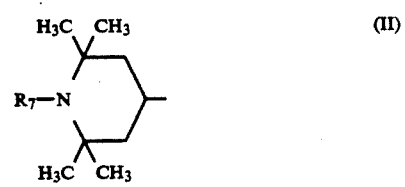

where $R_7$ is as defined for $R_1$, and $R_5$ and $R_6$ which can be identical or different are hydrogen, $C_1-C_{18}$alkyl, $C_5-C_{12}$cycloalkyl which is unsubstituted or mono-, di- or tri-substituted by $C_1-C_4$alkyl, $C_7-C_9$phenylalkyl which is unsubstituted or mono-, di- or tri-substituted by $C_1-C_4$alkyl, $C_7-C_9$phenylalkyl which is unsubstituted or mono-, di- or tri-substituted on the phenyl by $C_1-C_4$alkyl, $C_2-C_4$alkyl substituted in the 2-, 3- or 4-position by $C_1-C_8$alkoxy or by di-($C_1-C_4$alkyl)-amino, or a group of the formula (II), or the group

is a heterocyclic ring having 5–7 members, m is an integer from 2 to 6, and, if
m is 2, $R_3$ is one of the groups of the formula (IIIa)–(IIe)

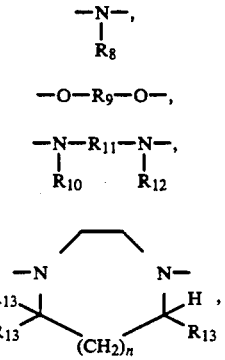

in which $R_8$, $R_{10}$, $R_{12}$ and $R_{14}$ which can be identical or different are hydrogen $C_1$–$C_{18}$alkyl, $C_5$–$C_{12}$cycloalkyl which is unsubstituted or mono-, di- or tri-substituted by $C_1$–$C_4$alkyl, $C_7$–$C_9$phenylalkyl which is unsubstituted or mono-, di-' or tri-substituted on the phenyl by $C_1$–$C_4$-alkyl, or a group of the formula (II), $R_9$ is $C_2$–$C_{12}$alkylene, cyclophenylene, cyclohexylenedimethylene, methylenedicyclohexylene, isopropylidenedicyclohexylene, phenylene or xylylene, $R_{11}$ is as defined for $R_9$ or is $C_4$–$C_{12}$alkylene interrupted by 1, 2 or 3 oxygen atoms, $R_{13}$ is hydrogen or methyl,
n is zero or 1 and, if m is 3, 4, 5 or 6, $R_3$ is a group of the formula (IV)

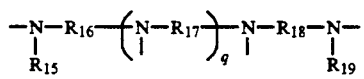

in which $R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and if m is 3, $R_3$ is also a group of the formula (Va) or (Vb)

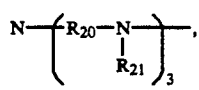

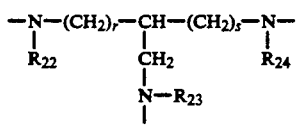

in which $R_{20}$ is $C_2$–$C_6$alkylene, $R_{21}$, $R_{22}$, $R_{23}$ and $R_{24}$ which can be identical or different are as defined for $R_8$, and r and s which can be identical or different are integers from 2 to 6.

2. A composition according to claim 1 wherein component (b) is a compound of formula I, where $R_1$ is hydrogen, $C_1$–$C_4$alkyl, OH, $C_6$–$C_{12}$alkoxy, $C_5$–$C_8$ cycloalkoxy, allyl, benzyl, acetyl or 2-hydroxyethyl.

3. A composition according to claim 1 wherein component (b) is a compound of formula I, where $R_2$ is a group —$OR_4$, —$SR_4$ or

in which $R_4$ is $C_1$–$C_{12}$alkyl, $C_5$–$C_8$cycloalkyl which is unsubstituted or mono-, di- or tri-substituted by $C_1$–$C_4$alkyl, phenyl, benzyl, $C_3$–$C_{12}$alkyl interrupted by 1 or 2 oxygen atoms, $C_2$–$C_3$alkyl substituted in the 2- or 3-position by di-($C_1$–$C_4$alkyl)-amino, or a group of the formula (II) and $R_5$ and $R_6$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, benzyl, $C_2$–$C_3$alkyl substituted in the 2- or 3-position by $C_1$–$C_4$alkoxy or by di-($C_1$–$C_4$alkyl)-amino, or a group of the formula (II), or the group

is 1-pyrrolidyl, 1-piperidyl, 4-morpholinyl, 4-methyl-1-piperazinyl or 1-hexahydro-azepinyl, m is an integer from 2 to 6 and, if m is 2, $R_3$ is one of the groups of the formula (IIIa)–(IIId) in which $R_8$, $R_{10}$ and $R_{12}$ which can be identical or different are hydrogen, $C_1$–$C_{12}$alkyl, $C_5$–$C_8$cycloalkyl which is unsubstituted or mono-, di- or tri-substituted by $C_1$–$C_4$alkyl, benzyl or a group of the formula (II), $R_9$ is $C_2$–$C_{10}$alkylene, cyclohexylene, cyclohexylenedimethylene, methylenedicyclohexylene, isopropylidenedicyclohexylene or xylylene, $R_{11}$ is as defined for $R_9$ or is $C_4$–$C_{10}$alkylene interrupted by 1 or 2 oxygen atoms, $R_{13}$ is hydrogen or methyl,
n is zero or 1, and, if m is 3, 4, 5 or 6, $R_3$ is a group of the formula (IV) in which
$R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and, if m is 3, $R_3$ can also be a group of the formula (Va) or (Vb) in which $R_{20}$ is $C_2$–$C_6$alkylene and $R_{21}$, $R_{22}$, $R_{23}$ and $R_{24}$ which can be identical or different are as defined for $R_8$, and r and s which can be identical or different are integers from 2 to 6.

4. A composition according to claim 1 wherein component (b) is a compound of formula I, where $R_2$ is a group —$OR_4$ or

in which $R_4$ is $C_1$–$C_{10}$alkyl, cyclohexyl which is unsubstituted or mono-, di- or tri-substituted by $C_1$–$C_4$alkyl, phenyl, benzyl or a group of the formula (II) and $R_5$ and $R_6$ which can be identical or different are hydrogen, $C_1$–$C_{10}$alkyl, cyclohexyl which is unsubstituted or mono-, di- or tri-substituted by $C_1$–$C_4$alkyl, benzyl, $C_2$–$C_3$alkyl substituted in the 2- or 3-position by methoxy, by ethoxy, by dimethylamino or by diethylamino, or a group of the formula (II), or the group

is 4-morpholinyl, m is an integer from 2 to 6 and, if m is 2, $R_3$ is one of the groups of the formula (IIIa)–(IIId) in which $R_8$, $R_{10}$ and $R_{12}$ which can be identical or different are hydrogen, $C_1$–$C_{10}$alkyl, cyclohexyl which is unsubstituted or mono-, di- or tri-substituted by $C_1$–$C_4$alkyl, benzyl or a group of the formula (II), $R_9$ is $C_2$–$C_8$alkylene, cyclohexylenedimethylene, methylenedicyclohexylene or xylylene, $R_{11}$ is as defined for $R_9$ or is $C_4$–$C_{10}$alkylene interrupted by 1 or 2 oxygen atoms, $R_{13}$ is hydrogen or methyl, n is zero or 1, and, if m is 3, 4, 5 or 6, $R_3$ is a group of the formula (IV) in which $R_{15}$ and $R_{19}$ which can be identical or different are as defined for $R_8$, and $R_{16}$, $R_{17}$ and $R_{18}$ which can be identical or different are $C_2$–$C_6$alkylene and q is zero, 1, 2 or 3, and, if m is 3, $R_3$ can also be a group of the formula (Va) or (Vb) in which $R_{20}$ is $C_2$–$C_3$alkylene, $R_{21}$, $R_{22}$, $R_{23}$ and $R_{24}$ which can be identical or different are as defined for $R_8$ and r and s which can be identical or different are integers from 3 to 5.

5. A composition according to claim 1 wherein component (b) is a compound of formula I, where $R_2$ is a group —$OR_4$ or

in which $R_4$ is $C_1$–$C_8$alkyl, cyclohexyl, phenyl, benzyl or a group of the formula (II) and $R_5$ and $R_6$ which can be identical or different are $C_1$–$C_8$alkyl, cyclohexyl, benzyl, $C_2$–$C_3$alkyl substituted in the 2- or 3-position by methoxy, by ethoxy, by dimethylamino or by diethylamino, or a group of the formula (II) or $R_5$ can also be hydrogen, or the group

is 4-morpholinyl, m is 2, 3 or 4 and, if m is 2, $R_3$ is one of the groups of the formula (IIIb)–(IIId) in which $R_{10}$ and $R_{12}$ which can be identical or different are hydrogen, $C_1$–$C_4$alkyl, cyclohexyl or a group of the formula (II), $R_9$ is $C_2$–$C_6$alkylene, $R_{11}$ is $C_2$–$C_6$alkylene, cyclohexylenedimethylene, methylenedicyclohexylene, xylylene or $C_4$–$C_{10}$alkylene interrupted by 1 or 2 oxygen atoms, $R_{13}$ is hydrogen, n is zero, and, if m is 3 or 4, $R_3$ is a group of the formula (IV) in which $R_{15}$ and $R_{19}$ which can be identical or different are as defined for $R_{10}$, and $R_{16}$, $R_{17}$ and $R_{18}$ which can be identical or different are $C_2$–$C_6$alkylene and q is zero of 1.

6. A composition according to claim 1 wherein component (b) is a compound of formula I, where $R_1$ is hydrogen or methyl, $R_2$ is a group —$OR_4$ or

in which $R_4$ is $C_1$–$C_4$alkyl, 2,2,6,6-tetramethyl-4-piperidyl or 1,2,2,6,6-pentamethyl-4-piperidyl and $R_5$ and $R_6$ which can be identical or different are $C_1$–$C_8$alkyl,
2,2,6,6-tetramethyl-4-piperidyl or 1,2,2,6,6-pentamethyl-4-piperidyl, or $R_5$ is hydrogen, or the group

is 4-morpholinyl, m is 2, 3 or 4, and if ma is 2, $R_3$ is one of the groups of the formula (IIIc) or (IIId) in which $R_{10}$ and $R_{12}$ which can be identical or different are hydrogen, methyl, isopropyl, cyclohexyl, 2,2,6,6-tetramethyl-4-piperidyl or 1,2,2,6,6-pentamethyl-4-piperidyl, $R_{11}$ is $C_2$–$C_6$alkylene or $C_6$–$C_{10}$alkylene interrupted by 2 oxygen atoms, $R_{13}$ is hydrogen, n is zero, and, if m is 3 or 4, $R_3$ is a group of the formula (IV) in which $R_{15}$ and $R_{19}$ which can be identical or different are as defined for $R_{10}$, and $R_{16}$ and $R_{18}$ which can be identical or different are $C_2$–$C_3$alkylene and q is zero or 1.

7. A composition according to claim 1 wherein component (b) is a compound of formula I, where $R_1$ is hydrogen or methyl, $R_2$ is 2,2,6,6-tetramethyl-4-piperidyloxy or 1,2,2,6,6-pentamethyl-4-piperidyloxy, m is 2, 3 or 4 and, if m is 2, $R_3$ is a group of the formula (IIIc) in which $R_{10}$ and $R_{12}$ which can be identical or different are hydrogen, cyclohexyl, 2,2,6,6-tetramethyl-4-piperidyl or 1,2,2,6,6-pentamethyl-4-piperidyl, $R_{11}$ is $C_2$–$C_6$alkylene, and, if m is 3 or 4, $R_3$ is a group of the formula (IV) in which $R_{15}$ and $R_{19}$ which can be identical or different are hydrogen, 2,2,6,6-tetramethyl-4-piperidyl or 1,2,2,6,6-pentamethyl-4-piperidyl, $R_{16}$, $R_{17}$ and $R_{18}$ which can be identical or different are $C_2$–$C_3$alkylene and q is zero or 1.

8. A composition according to claim 1 wherein component (b) is a compound of the formula

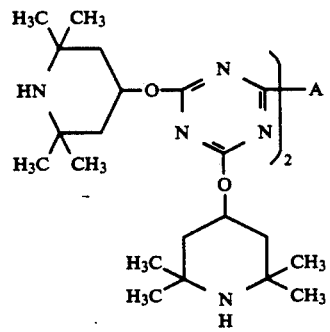

wherein A is a group

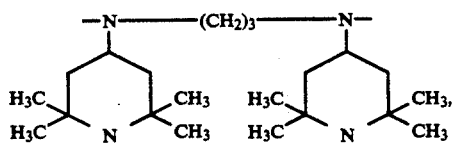

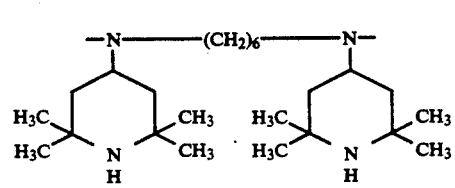

or

-continued

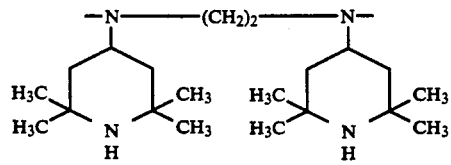

or a compound of the formula

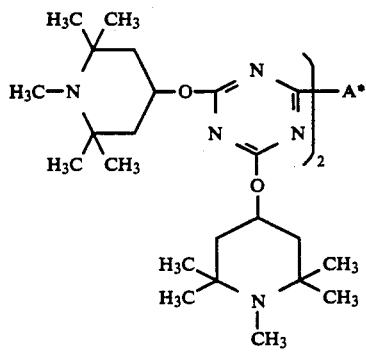

wherein A* is a group

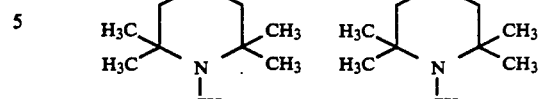

or

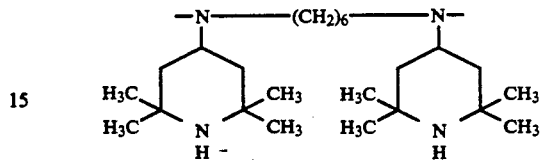

9. A composition according to claim 1, wherein the organic material is a synthetic polymer.

10. A composition according to claim 9 which, in addition to the compound of the formula (I), also contains other conventional additives for synthetic polymers.

11. A composition according to claim 1, wherein the organic material is a polyolefin.

12. A composition according to claim 1, in which the organic material is polyethylene or polypropylene.

13. A method for stabilizing an organic material against degradation induced by light, heat or oxidation, which method comprises incorporating in said organic material an effective stabilizing amount of a compound of the formula (I) according to claim 1.

* * * * *